(12) United States Patent
Kienle et al.

(10) Patent No.: US 7,109,487 B2
(45) Date of Patent: Sep. 19, 2006

(54) PARTICLE BEAM DEVICE

(75) Inventors: Martin Kienle, Ellwangen (DE); Helmut Muller, Schwabisch Gmund (DE); Peter Hoffrogge, Oberkochen (DE); Wilhelm Bolsinger, Dischingen (DE)

(73) Assignee: Carl Zeiss NTS GmbH, Oberkochen (DE)

( * ) Notice: Subject to any disclaimer, the term of this patent is extended or adjusted under 35 U.S.C. 154(b) by 0 days.

(21) Appl. No.: 10/974,000

(22) Filed: Oct. 26, 2004

(65) Prior Publication Data

US 2005/0116165 A1 Jun. 2, 2005

(30) Foreign Application Priority Data

Oct. 31, 2003 (DE) ................ 103 51 276

(51) Int. Cl.
*G01N 23/00* (2006.01)
(52) U.S. Cl. .............. 250/311; 250/310; 250/307; 250/492.2; 250/440.11; 118/723 FI; 156/345.39
(58) Field of Classification Search ........... 250/311, 250/310, 307; 118/723 FI; 156/345.39
See application file for complete search history.

(56) References Cited

U.S. PATENT DOCUMENTS

| | | | |
|---|---|---|---|
| 4,645,929 A | 2/1987 | Criegern | |
| 5,770,861 A | 6/1998 | Hirose et al. | |
| 5,986,264 A | 11/1999 | Grünewald | |
| 6,002,128 A | 12/1999 | Hill et al. | |
| 6,080,991 A * | 6/2000 | Tsai | 250/492.21 |
| 6,497,194 B1 * | 12/2002 | Libby et al. | 118/723 FI |
| 6,781,125 B1 * | 8/2004 | Tokuda et al. | 250/310 |

2002/0050565 A1 5/2002 Tokuda et al.

FOREIGN PATENT DOCUMENTS

| | | |
|---|---|---|
| DE | 3403254 A1 | 1/1984 |
| DE | 295 07 225 U1 | 4/1995 |
| DE | 196 08 082 A1 | 3/1996 |
| EP | 0 824 759 B1 | 4/1996 |

OTHER PUBLICATIONS

Computer translation of JP 05041195 A (8 pages) from the Japanese Patent Office Website.
Animate CrossBeam® Tour; "LEO 1500 CrossBeam® Workstation" (1 page); www.zeiss.de (section semiconductor technology/material analysis).
Abstract for Japanese Application No. 04233149 A; publication date Aug. 21, 1992.
Abstract for Japanese Application No. 05041195 A; publication date Feb. 19, 1993.
Abstract for Japanese Application No. 04277456 A; publication date Oct. 2, 1992.

* cited by examiner

*Primary Examiner*—Jack Berman
*Assistant Examiner*—Zia R. Hashmi
(74) *Attorney, Agent, or Firm*—Muirhead & Saturnelli, LLC

(57) ABSTRACT

A particle beam device, in particular an electron microscope, having at least two particle beam columns and one object slide having a receiving surface for receiving an object. The particle beam device makes it possible to align the surface of the object perpendicular to the beam axes of the particle beam columns, using simple means, in an accurate and error-free manner. The object slide assumes a basic position from which it may be tilted into the position in which the first or the second beam axis is perpendicular or at least almost perpendicular to the receiving surface of the object slide. In the basic position, a normal to the receiving surface of the object slide is spatially oriented such that an angle formed between the first beam axis and the normal is greater than or equal to an angle formed between the second beam axis and the normal.

18 Claims, 4 Drawing Sheets

PARTICLE BEAM DEVICE

FIELD OF THE INVENTION

The present invention relates to a particle beam device and method and, in particular, an electron microscope.

BACKGROUND OF THE INVENTION

Electron beam devices, in particular scanning electron microscopes, are used for examining surfaces of objects (samples). For example in the case of a scanning electron microscope, an electron beam generated by a beam generator is focused by an objective lens for focusing onto the object to be examined. A deflector is used to direct the electron beam (subsequently also referred to as the primary electron beam) over the surface of the object to be examined, thereby scanning the surface. The electrons of the primary electron beam interact with the object in this process. As a result of this interaction, in particular electrons are emitted from the object (secondary electrons) or electrons of the primary electron beam are backscattered (backscattered electrons). Secondary and backscattered electrons form the secondary beam and are detected via a detector. The thus generated detector signal is used for image generation.

It is also known to equip a scanning electron microscope with an ion beam column. Ions used for preparing objects (e.g., polishing the object or depositing material on the object) or also for imaging are generated via an ion beam generator situated in the ion beam column. The applicant markets such a scanning electron microscope, which is available under the name "LEO CROSSBEAM".

To achieve the greatest electron-optical resolution, the primary electron beam must be delivered perpendicular to the surface of the object to be examined. Vertical ion irradiation is also desirable to achieve uniform preparation of the object. FIG. 1 shows a system previously used by the applicant in a scanning electron microscope. Situated in the scanning electron microscope is an electron beam column 2, its beam axis 24 corresponding to the vertical line. An ion beam column 3 having a beam axis 25 is also provided. Beam axis 25 is tilted at an angle $2\alpha$ with respect to beam axis 24. Beam axis 24 and beam axis 25 meet on a receiving surface 5 of an object slide 4 at a point of coincidence. To obtain the best electron-optical resolution or best preparation via the ion beam, object slide 4 is tilted in such a way that either beam axis 24 or beam axis 25 is perpendicular to receiving surface 5 of object slide 4.

Subsequently, object slide 4 must be tilted at an angle $2\alpha$ to be moved from one position to another. This is a particularly large tilt angle. However, the greater the tilt angle, the less precise and error-prone the perpendicularity of receiving surface 5, i.e., the surface of the object to the ion beam or primary electron beam, in particular due to mechanical forces.

A tilting mechanism which also has these disadvantages is known from DE 196 08 082 A1. This publication relates to an ion beam preparation device for processing samples for electron microscopy. A preparation process is observed using a scanning electron microscope. The optical axis of the scanning electron microscope is aimed at a sample positioned in a sample holder. The known device also has an ion source aimed at the sample, the sample holder and the ion source being situated about the central rotational axis so that they are tiltable with respect to one another.

Accordingly, it is desirable to provide a particle beam device which makes it possible, using simple means, to align the object surface perpendicular to the beam axes of the particle beam columns in the most accurate and error-free manner possible.

SUMMARY OF THE INVENTION

A particle beam device according to certain embodiments of the present invention typically has at least one first particle beam column having a first beam axis and at least one second particle beam column having a second beam axis. The first and the second particle beam axes are situated in such a way that their beam axes form an angle. The particle beam device also has an object slide including a receiving surface which is able to be tilted into such a position that the first or the second beam axis is perpendicular or at least almost perpendicular to the receiving surface of the object slide. The object slide assumes a basic position from which it is able to be tilted into the position in which the first or the second beam axis is perpendicular or at least almost perpendicular to the receiving surface of the object slide. In the basic position, a normal to the receiving surface of the object slide is spatially oriented in such a way that the absolute value of an angle formed between the first beam axis and the normal is greater than or equal to an angle formed between the second beam axis and the normal, this angle not equaling 0°.

In the case of the particle beam device according to some embodiments the present invention, the object to be examined may be tilted from the basic position of the object slide into the positions (subsequently referred to as the examination/processing positions) in which the beam axes of the two particle beam columns are perpendicular or almost perpendicular to the surface of the object. The examination/processing positions do not match the basic position in this context. Moreover, the object slide assumes the basic position at least temporarily when being tilted from one examination/processing position to another.

The particle beam device according to some embodiments of the present invention has the advantage that, starting from the basic position, only a small tilt angle is necessary to reach an examination/processing position. This results in a significant reduction in mechanical inaccuracies when assuming the examination/processing position. The smaller the angle by which the object slide is to be tilted, the fewer errors result from given mechanical conditions of a tilt bearing (pivot bearing) during adjustment in the tilt direction. For example, when adjusting a tilt about a first axis, even undesired, minor tilting may occur about a second axis. This only occurs minimally or not at all if the tilt angle of the object slide is small. Due to the smaller tilt angle and a consequently shorter lever arm, the force to be applied to tilt the object slide into one of the examination/processing positions is less than in the related art. As a result, smaller forces act on the tilt bearing during tilting and in the examination/processing positions. In contrast, higher forces act on the tilt bearing in the related art and counteract the tilt motion. When using the related art in an electron microscope, the image may drift when observing one point of an object for an extended period.

It is preferably provided for the normal to correspond to the bisector of the angle formed by the first and the second beam axis. As a result of this symmetrical configuration, the object slide must be tilted in each case by the same angle for assuming the examination/processing positions from the basic position. This type of configuration significantly simplifies operation since tilting must always only be performed by a certain, predefined angle. Moreover, the error-prone tilt path is reduced by half in comparison with the known devices.

The first and the second particle beam columns are preferably situated on a vacuum chamber in which the object slide is accommodated. For example, this is the case for electron microscopes in particular. It is also advantageous to accommodate the first and the second particle beam columns at least partially in the vacuum chamber. It is also provided for the first and the second particle beam columns to be situated in such a way that their beam axes are tilted at an angle preferably symmetrically with respect to the vertical. This angle is greater than 10°, preferably in a range between 10° and 40°.

In a preferred embodiment of the present invention, the first and the second particle beam columns are attached to the top of the vacuum chamber. This has the particular advantage that vibrations occurring in the vacuum chamber are transferred equally to the object slide and the particle beam columns, i.e., in particular to an electron column and an ion column, thereby resulting in movements in the same directions having no disrupting influence on the optical quality of the particle beam device, in particular of a scanning electron microscope.

According to a further embodiment of the present invention, the object slide is supported by a tilt bearing and connected to the vacuum chamber, in particular to a top of the vacuum chamber via a connecting bar. Vibrations occurring in the vacuum chamber are transferred equally in this manner to the object slide and the particle beam columns. Motions that do not influence the optical quality occur in the same directions also in this instance.

The first particle beam column preferably has a first beam generator for generating a first particle beam and a first beam guiding system for guiding the first particle beam, while the second particle beam column has a second beam generator for generating a second particle beam and a second beam guiding system for guiding the second particle beam. Furthermore, each of the two beam guiding systems has an objective lens for focusing the first and the second particle beams, respectively, on the object slide.

The first particle beam column is preferably designed as an electron beam column, and the second particle beam column is preferably designed as an ion beam column. The second particle beam column may also be designed as an electron beam column and the first particle beam column may also be designed as an ion beam column.

The present invention also relates to an electron microscope, in particular to a scanning electron microscope or also to a transmission electron microscope, having at least one of the features or feature combinations recited above.

Furthermore, the particle beam device may be preferably designed as a scanning electron microscope. The particle beam device according to some embodiments of the present invention has at least one first particle beam column including a first beam axis as well as at least one second particle beam column including a second beam axis. The first and the second particle beam columns are situated in such a way that their beam axes form an angle. Also provided is an object slide which has a receiving surface and is able to be tilted into such a position that the first or the second beam axis is perpendicular or at least almost perpendicular to the receiving surface of the object slide. The first and the second beam axes are tilted with respect to the vertical at an angle greater than 10°. In a particular embodiment, the angle is in a range between 10° and 40°, preferably between 15° and 35°, and particularly preferably in the range between 20° and 30°. The angles at which the two beam axes are tilted with respect to the vertical may be equal or different. The particle beam device according to various embodiments of the present invention may also have at least one feature or a combination of features already explained above.

BRIEF DESCRIPTION OF THE DRAWINGS

The present invention is explained in greater detail below on the basis of exemplary embodiments and the drawings, in which.

DETAILED DESCRIPTION OF VARIOUS EMBODIMENTS

Figure 1:
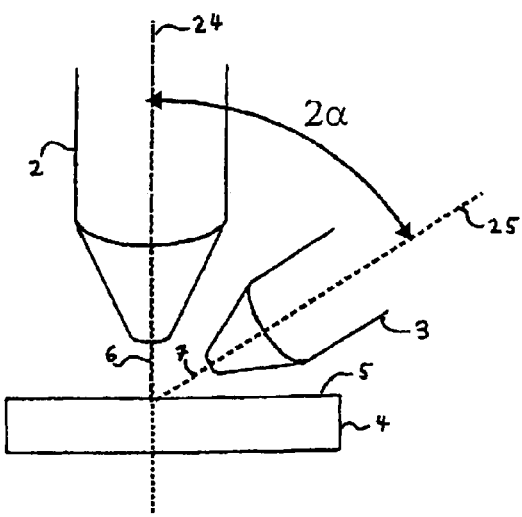
FIG. 1 schematically shows a particle beam device according to the related art.

The related art was already illustrated above on the basis of FIG. 1. The present invention is explained in greater detail below on the basis of FIGS. 2 through 6 which have the above-mentioned advantages.

Figure 2:
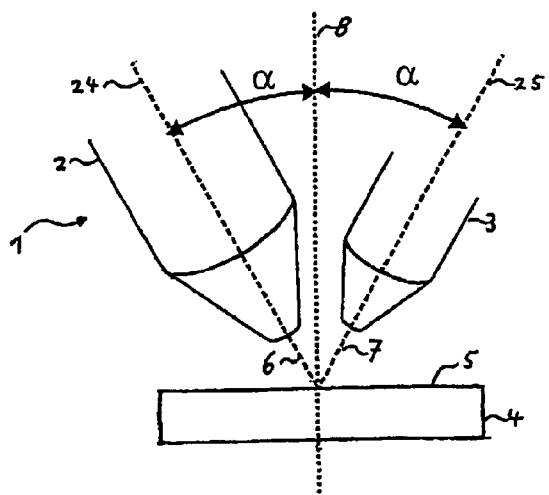
FIG. 2 schematically shows the particle beam device according to one embodiment of the present invention having the object slide in the basic position.

FIG. 2 schematically shows a particle beam device 1 according to one embodiment of the present invention. It has two particle beam columns 2 and 3, their beam axes 24 and 25 being situated symmetrically at an angle α with respect to vertical line 8, which is perpendicular to a receiving surface 5 of an object slide 4. Object slide 4 is in the basic position shown in FIG. 2 from which certain tilt positions of object slide 4 are settable with respect to beam axes 24 and 25 at predefined tilt angles. Object slide 4 may be tilted from this basic position into the above-described examination/processing positions.

Figure 3:
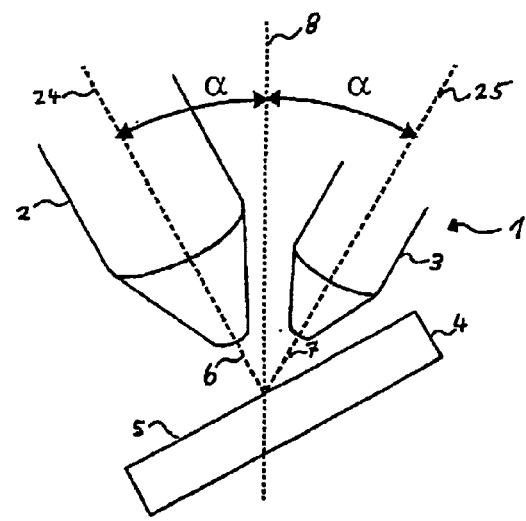
FIG. 3 schematically shows the particle beam device according to FIG. 2 having the object slide in an examination/processing position.

FIG. 3 shows one of the two examination/processing positions. Object slide 4 is tilted from the basic position by an angle α in such a way that beam axis 24 is perpendicular to the surface of the object situated on object slide 4. In this position, particles 6 generated in particle beam column 2 impinge almost vertically on the object. Object slide 4 may be tilted from this position into the other examination/processing position in that it assumes the basic position at least temporarily. This achieves the advantages recited in more detail above.

Figure 4A:
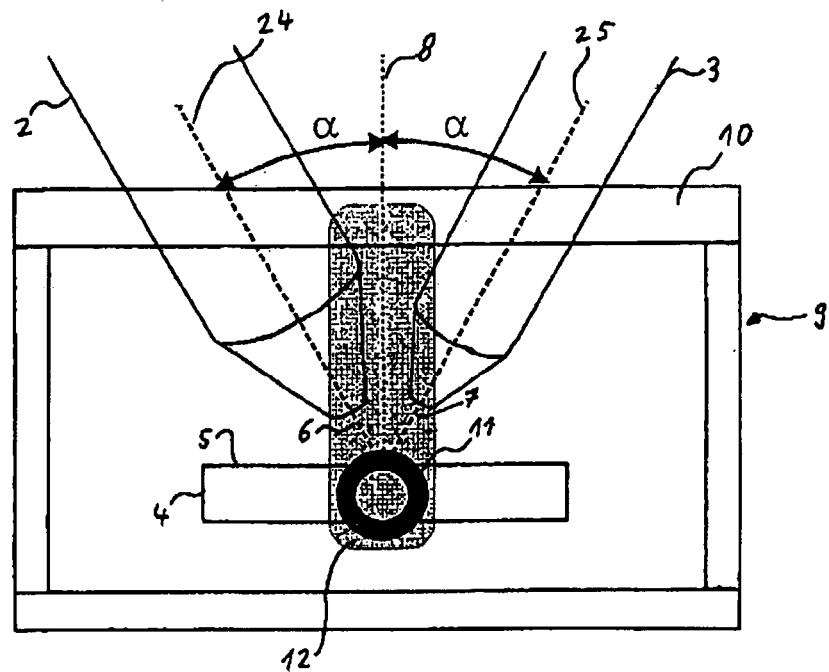
FIGS. 4a–b schematically show two embodiments of the particle beam device according to the present invention in connection with a vacuum chamber.

FIG. 4a schematically shows a further advantageous embodiment of the present invention as it may be realized in particular in a scanning electron microscope. Identical reference numerals relate to identical components recited above. The scanning electron microscope has a vacuum chamber 9, the two particle beam columns 2 and 3 being attached to its top 10 in such a way that they protrude into vacuum chamber 9. An object slide 4 is attached in vacuum chamber 9 to a tilt bearing 11, which is attached to a connecting bar 12, which is connected to top 10 of vacuum chamber 9, object slide 4 shown in FIG. 4a assuming the above-described basic position. The connection of object slide 4 to top 10 of vacuum chamber 9 ensures particularly high stability. As a result, occurring vibrations, e.g., building vibrations, are transferred equally to object slide 4 and particle beam columns 2 and 3. Movements result in the same direction and do not negatively affect the image quality.

Figure 4B:
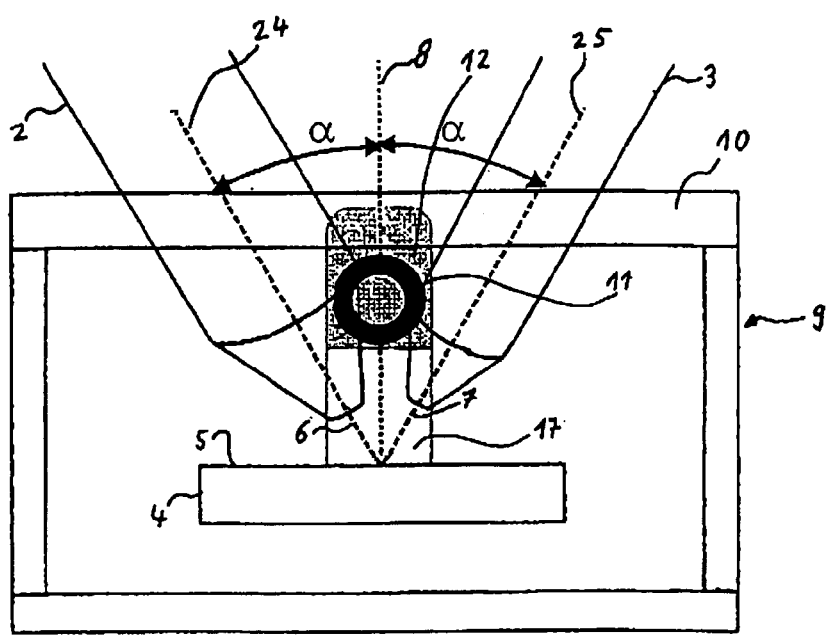

FIG. 4b shows a further embodiment of the present invention which basically corresponds to the embodiment of FIG. 4a. In contrast to the embodiment in FIG. 4a, object slide 4 is not attached to a tilt bearing 11 in the embodiment according to FIG. 4b but to a connecting element 17, which is connected to a connecting bar 12 via a tilt bearing 11. Connecting bar 12 is then attached to top 10 of vacuum chamber 9.

Figure 5:
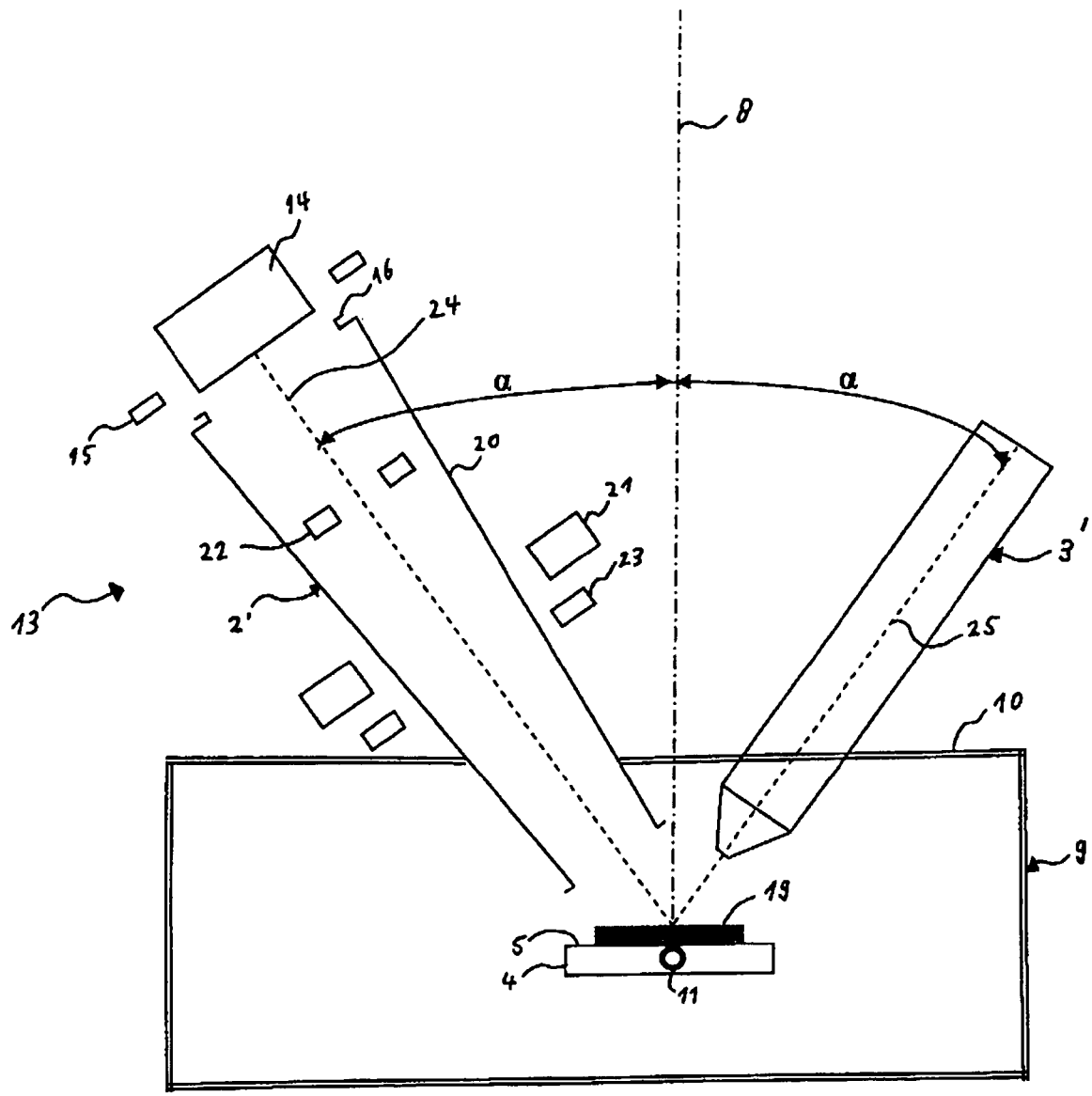
FIG. 5 schematically shows a section of a scanning electron microscope according to one embodiment of the present invention.

FIG. 5 schematically shows the present invention on the basis of the example of a scanning electron microscope 13 having a particle beam column 2' in the form of an electron beam column. Electron beam column 2' includes a beam generator in the form of an electron source 14 (cathode), an extraction electrode 15, as well as an anode 16, which also forms an end of a beam guide tube 20. Electron source 14 is preferably a thermal field emitter. Electrons emitted from electron source 14 are accelerated to an anode potential due to a potential difference between electron source 14 and anode 16 and form a primary electron beam. A lens 21 which functions as an objective and may be designed as a purely electrostatic lens, a purely magnetic lens, or as a combination of an electrostatic lens and a magnetic field (electrostatic-magnetic objective lens) is used to focus the primary electron beam, which is not shown here in greater detail, on examination object 19 which is situated on receiving surface 5 of object slide 4. The primary electron beam is directed in a grid pattern over the surface of examination object 19 via a deflection system 23. The electrons of the primary electron beam interact with the object in this process. As a result of the interaction, electrons in particular are emitted from the object (secondary electrons) or electrons of the primary electron beam are backscattered (backscattered electrons). Secondary and backscattered electrons form the secondary beam and are detected by a detector 22. The detector signal generated in this manner is used for image generation. Electron beam column 2' is attached to a top 10 of a vacuum chamber 9 and protrudes into vacuum chamber 9.

In addition to electron beam column 2', scanning electron microscope 13 has a particle beam column 3' in the form of an ion beam column which is also attached to top 10 of vacuum chamber 9. Ion beam column 3' also protrudes into vacuum chamber 9 and has means for ion beam generation and ion beam guiding which are not shown in greater detail here.

In the embodiment of the scanning electron microscope shown here, both particle beam columns 2' and 3' are situated symmetrically at a certain angle α with respect to vertical line 8, which is perpendicular to receiving surface 5 of object slide 4. In the position according to FIG. 5, object slide 4 including object 19 are in the above-described basic position from which object slide 4 or object 19 is tiltable into two examination/processing positions.

In one position, beam axis 24 of electron beam column 2' is perpendicular to the surface of object 19 or to receiving surface 5 of object slide 4. In this position, object 19 is scanned by the primary electron beam and an image is generated in the manner known from the related art. In the other position, beam axis 25 of ion beam column 3' is perpendicular to the surface of object 19 or to receiving surface 5 of object slide 4. To move from one position to the other, object slide 4 is tilted, the basic position being temporarily assumed, thereby achieving the above-described advantages.

Figure 6:
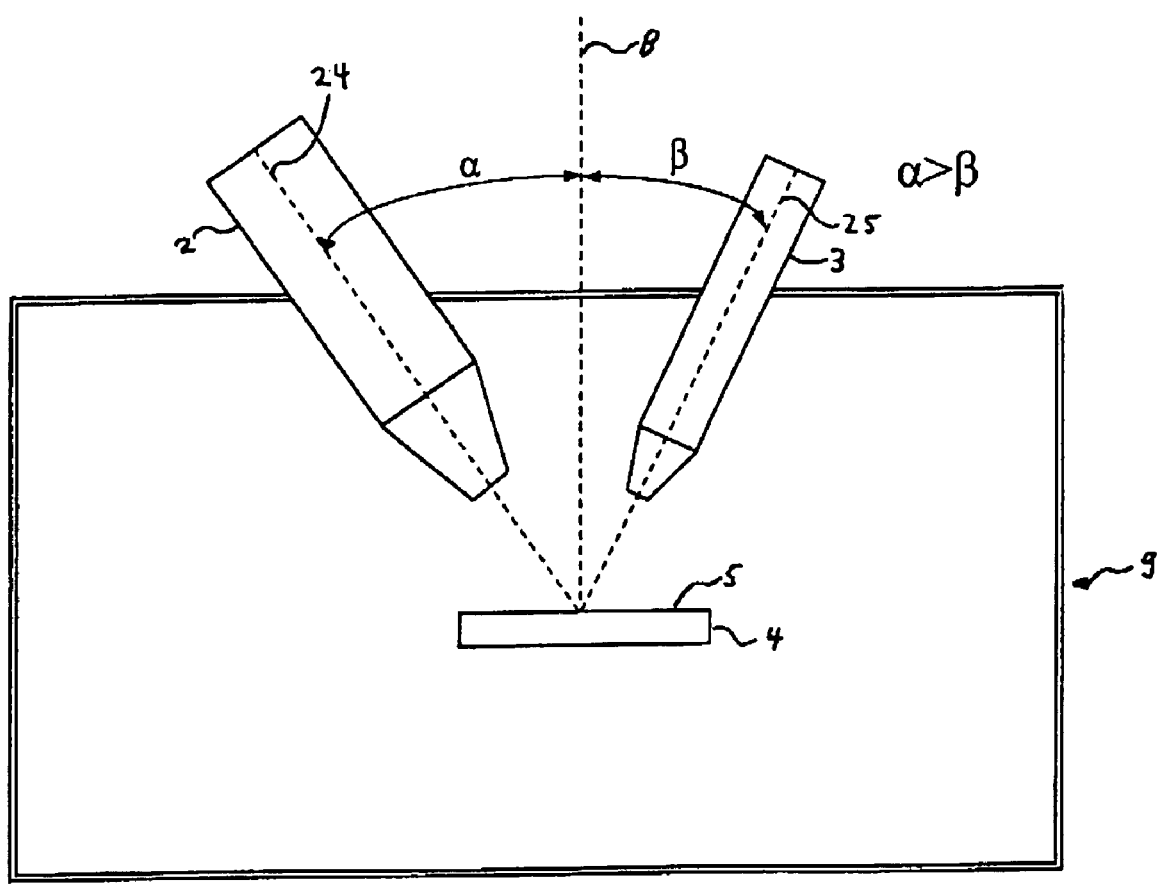
FIG. 6 schematically shows a further embodiment of the particle beam device according to the present invention having asymmetrically situated particle beam columns.

FIG. 6 shows a further exemplary embodiment of a particle beam device according to the present invention having two particle beam columns 2 and 3, which are attached to a vacuum chamber 9 and protrude into vacuum chamber 9. An object slide 4, which assumes a basic position in which vertical line 8 is perpendicular to a receiving surface 5 of object slide 4, is situated in vacuum chamber 9. Particle beam column 2 is situated in such a way that its beam axis 24 is tilted at an angle α with respect to vertical line 8. In contrast, particle beam column 3 is situated in such a way that beam axis 25 is tilted at angle β in the opposite direction to particle beam column 2. The absolute value of angle β is smaller than that of angle α. This embodiment also has the already recited advantages of the present invention. Starting from the basic position, only smaller tilt angles are necessary to reach the examination/processing position. This means a significant reduction in mechanical inaccuracies when assuming the examination/processing position. The smaller the tilt angle by which the object slide is to be tilted, the fewer errors result from given mechanical conditions of the pivot bearing during the adjustment in the tilt direction. Moreover, weaker forces act on the pivot bearing so that the above-mentioned image drift is reduced or even eliminated, resulting in improved image stability.

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

What is claimed is:

1. A particle beam device, comprising:
   at least one first particle beam column having a first beam axis;
   at least one second particle beam column having a second beam axis, the first and the second particle beam columns being situated in such a way that their beam axes form an angle; and
   an object slide having a receiving surface which can be tilted into such a position that the first or the second beam axis is substantially perpendicular to the receiving surface of the object slide, wherein the first and the second beam axes are tilted with respect to the vertical by an angle which is in a range between 15° and 35°.

2. The particle beam device as recited in claim 1, wherein the first and the second particle beam columns are attached to a vacuum chamber in which the object slide is situated.

3. The particle beam device as recited in claim 2, wherein the first and the second particle beam columns are at least partially situated in the vacuum chamber.

4. The particle beam device as recited in claim 2, wherein the first and the second particle beam columns are attached to a top of the vacuum chamber.

5. The particle beam device as recited in claim 2, wherein the object slide is attached to a tilt bearing and connected to the vacuum chamber via a connecting bar.

6. The particle beam device as recited in claim 5, wherein the object slide is connected to a top of the vacuum chamber via the connecting bar.

7. The particle beam device as recited in claim 1, wherein the first particle beam column has a first beam generator for generating a first particle beam and a first beam guiding system for guiding the first particle beam, and the second particle beam column has a second beam generator for generating a second particle beam and a second beam guiding system for guiding the second particle beam.

8. The particle beam device as recited in claim 7, wherein the first beam guiding system and the second beam guiding system each have an objective lens for focusing the first and the second particle beams, respectively, on the object slide.

9. The particle beam device as recited in claim 1, wherein the first particle beam column is an electron beam column and the second particle beam column is an ion beam column.

10. An electron microscope, in particular a scanning electron microscope, which is configured as a particle beam device as recited in claim 9.

11. The particle beam device as recited in claim 1, wherein the angle by which the first or the second beam axis is tilted with respect to the vertical is in the range between 20° and 30°.

12. The particle beam device as recited in claim 1, wherein the angles by which both beam axes are tilted with respect to the vertical are equal.

13. A particle beam device, comprising:
   at least one first particle beam column having a first beam axis;
   at least one second particle beam column having a second beam axis, wherein the beam axes of the first and the second particle columns form an angle; and
   an object slide having a receiving surface which can be tilted into such a basic position that the first or the second beam axis is substantially perpendicular to the receiving surface of the object slide, and, in the basic position, a normal to the receiving surface is spatially oriented in such a way that an angle formed between the first beam axis and the normal is greater than or equal to an angle formed between the second beam axis and the normal, and wherein the first and the second beam axes are tilted with respect to the vertical by an angle which is in a range between 15° and 35°.

14. The particle beam device as recited in claim 13, wherein the first and the second particle beam columns are attached to a vacuum chamber in which the object slide is situated.

15. The particle beam device as recited in claim 13, wherein the first particle beam column has a first beam generator for generating a first particle beam and a first beam guiding system for guiding the first particle beam, and the second particle beam column has a second beam generator for generating a second particle beam and a second beam guiding system for guiding the second particle beam.

16. The particle beam device as recited in claim 15, wherein the first beam guiding system and the second beam guiding system each have an objective lens for focusing the first and the second particle beams, respectively, on the object slide.

17. A method for operating a particle beam device, comprising:
   generating a first particle beam in a first particle beam column having a first beam axis;
   generating a second particle beam in a second particle beam column having a second beam axis, wherein the first and second particle beam columns are situated such that their beam axes form an angle; and
   tilting a receiving surface of an object slide from a basic position into a position, wherein in said position the first or the second beam axis is substantially perpendicular to the receiving surface of the object slide and wherein in said basic position a normal to the receiving surface is spatially oriented in such a way that an angle formed between the first beam axis and the normal is greater than or equal to an angle formed between the second beam axis and the normal, and further comprising tilting the first and second beam axes with respect to the vertical by an angle which is in a range between 15° and 35°.

18. The method of claim 17, wherein the first particle beam is an electron beam and the second particle beam is an ion beam.

* * * * *